United States Patent
Stupak

(10) Patent No.: US 8,821,497 B2
(45) Date of Patent: Sep. 2, 2014

(54) METHOD AND APPARATUS FOR MAXILLO-MANDIBULAR FIXATION

(76) Inventor: Howard D. Stupak, Southport, CT (US)

(*) Notice: Subject to any disclaimer, the term of this patent is extended or adjusted under 35 U.S.C. 154(b) by 807 days.

(21) Appl. No.: 12/912,549

(22) Filed: Oct. 26, 2010

(65) Prior Publication Data

US 2011/0098752 A1  Apr. 28, 2011

Related U.S. Application Data

(60) Provisional application No. 61/400,934, filed on Aug. 4, 2010, provisional application No. 61/338,192, filed on Feb. 16, 2010, provisional application No. 61/279,894, filed on Oct. 27, 2009.

(51) Int. Cl.
- *A61F 2/46* (2006.01)
- *A61B 17/04* (2006.01)
- *A61B 17/84* (2006.01)
- *A61F 2/08* (2006.01)
- *A61B 17/86* (2006.01)

(52) U.S. Cl.
CPC ......... *A61B 17/8685* (2013.01); *A61B 17/8625* (2013.01); *A61B 17/842* (2013.01)
USPC .......................................... 606/86 R; 606/300

(58) Field of Classification Search
USPC ......... 606/300, 301, 304, 309, 310, 311, 312, 606/320, 86 R, 28, 281, 283, 285, 286, 280; 433/18–20, 174; 128/898
See application file for complete search history.

(56) References Cited

U.S. PATENT DOCUMENTS

| | | | | |
|---|---|---|---|---|
| 4,468,200 A | * | 8/1984 | Munch | 433/174 |
| 4,813,869 A | * | 3/1989 | Gatewood | 433/18 |
| 4,872,449 A | * | 10/1989 | Beeuwkes, III | 602/5 |
| 4,968,248 A | * | 11/1990 | McColgan et al. | 433/18 |
| 5,082,445 A | * | 1/1992 | Singer | 433/169 |
| RE34,249 E | * | 5/1993 | Divis et al. | 433/18 |
| 8,118,850 B2 | | 2/2012 | Marcus | |
| 8,168,850 B2 | | 5/2012 | Gurtner et al. | |
| 2009/0036889 A1 | * | 2/2009 | Callender | 606/55 |

* cited by examiner

*Primary Examiner* — Anu Ramana
(74) *Attorney, Agent, or Firm* — Schwabe, Williamson & Wyatt

(57) ABSTRACT

Apparatus and method of use which can be used to immobilize maxilla and mandible in dental occlusion utilizing the tissue of the interdental space.

3 Claims, 3 Drawing Sheets

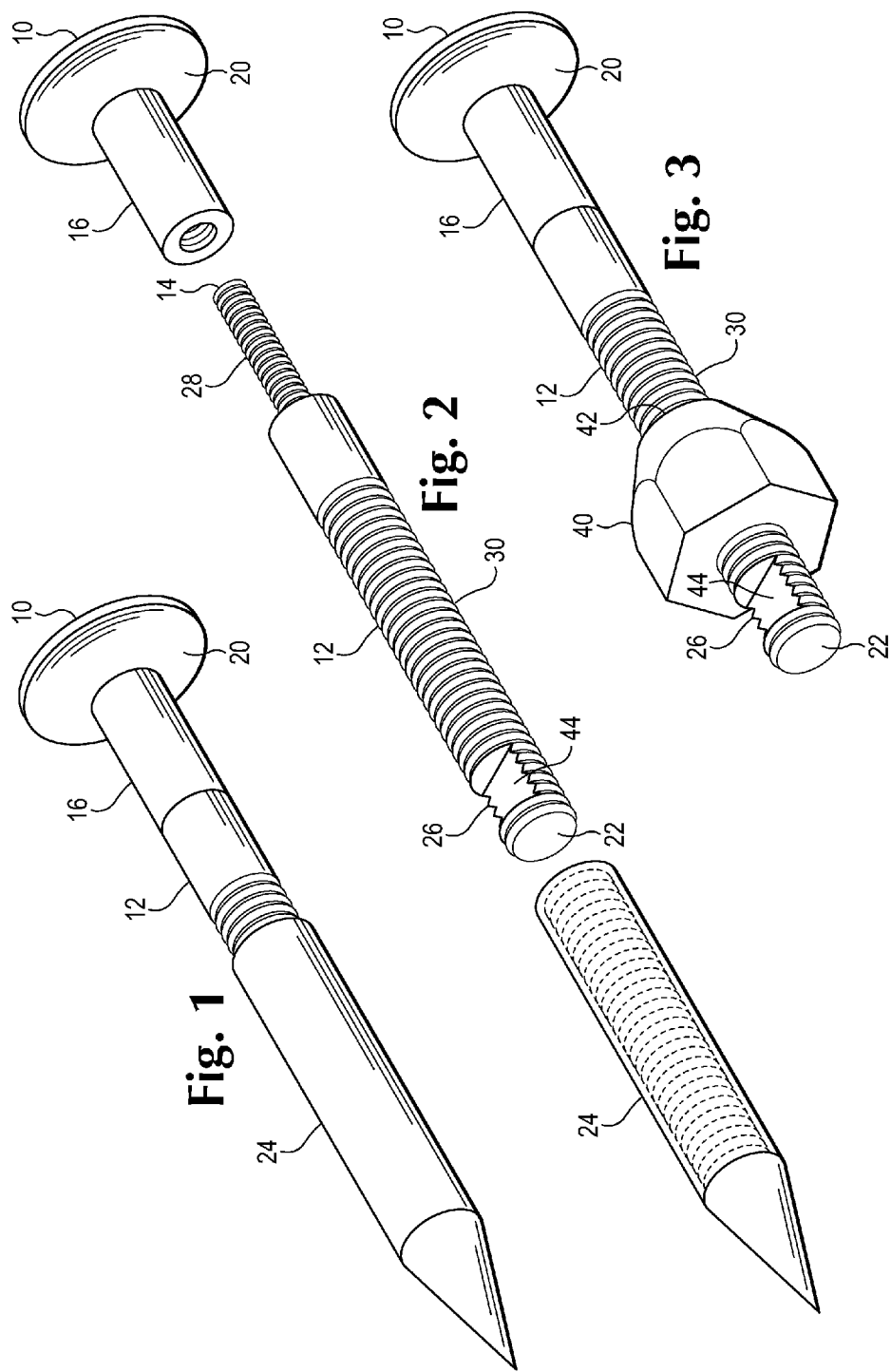

METHOD AND APPARATUS FOR MAXILLO-MANDIBULAR FIXATION

CROSS-REFERENCE TO RELATED APPLICATIONS

This application claims the benefit of U.S. Provisional Application Nos. 61/400,934, filed Aug. 4, 2010, 61/338,192, filed Feb. 16, 2010, and 61/279,894, filed Oct. 27, 2009.

BACKGROUND OF THE INVENTION

1. Field of Invention

The present invention is designed to treat mandible and facial fractures by improving the technique of maxillo-mandibular fixation (MMF) or intermaxillary fixation (IMF).

2. Prior Art

Those skilled in the art of treating fractures of the mandible are familiar with the current techniques in repairing mandible and other facial fractures. Most mandible fracture repairs require immobilization of the jaws in dental occlusion during healing. Achieving stable maxilla-mandibular fixation requires immobilization of the powerful jaw muscles using points of fixation which are strong enough to resist considerable force.

Stable immobilization of the jaws in dental occlusion is achieved by affixing the mandibular to the maxillary teeth (maxillo-mandibular fixation or MMF) Standard maxillo-mandibular fixation is achieved through arch bars wired to multiple teeth with circum-dental wires. Wires are wrapped around the base of each tooth, then those wires are attached to arch bars which approximate the mandibular and maxillary arches. The maxillary and mandibular arch bars subsequently may be wired together. The fixation strength provided by each wire wrapped around each individual tooth is relatively weak, and so substantially all of the teeth are wired so that they collectively provide sufficient strength. However, this wiring technique can be very time-consuming, tedious, and dangerous to surgeons, presenting a real risk of needle sticks and torn gloves. Moreover, it results in a fairly elaborate wiring scheme which can only be released with wire cutters. If a patient vomits, the jaws must be very quickly freed using wire cutters in order to protect the patient's airway. For this reason, the technique poses a real risk of asphyxiation if a patient or care taker is unable to free the jaws in time. There is also a significant risk that a patient will aspirate cut wire either during an emergency release or during the routine installation or removal of the wires.

An alternative technique to arch bar wiring MMF includes the use of screws placed in the cortical bone of the jaw between the tooth-roots as disclosed in U.S. patent application Ser. No. 12/329,263 with holes in the screw-head for wiring. These screws provide adequate fixation strength to resist the jaw muscles because they are driven through dense cortical bone. However, while this technique is faster, there is risk of injury to the toothroots, which would result in tooth death. The level of force required to drive screws into cortical bone, either with a pilot hole or without, is considerable, resulting in a relatively difficult and uncomfortable procedure for the patient. The screws must be placed using instruments such as drills, punches, screw drivers, etc., and many of these instruments are difficult to use within the confines of the mouth, restricting the available angles of approach. The screws can complicate the repair of jaw fractures. Moreover, the technique results in a less stable fixation than arch bar wiring MMF because the points of fixation on the respective jaws are significantly further apart from one another, permitting play in the wires, especially if stretched over time. Additionally, the risk of aspiration with wire-cutter failure remains.

Thus, the traditional methods of immobilizing jaws in dental occlusion for fracture repair have substantial drawbacks. However, those of skill in this art continue to use these methods despite their drawbacks because the conventional wisdom teaches that only the teeth in aggregate and the cortical bone of the jaw permit fixation that is strong enough to resist the jaw muscles. The interdental tissues have always been considered too weak to use for this purpose.

SUMMARY OF THE INVENTION

A first aspect of the invention is a method of immobilizing a maxilla and a mandible in occlusion comprising providing at least two members, each said member including a shaft having a diameter, a proximal end, and a distal end, a base affixed to said distal end, said base having a diameter which is larger than said diameter of said shaft, and each said member further including a connective structure located at said proximal end; inserting one said member through a first interdental space within said mandible; inserting another said member through a first interdental space within said maxilla; attaching a fastener to the proximal end of each said shaft; placing said mandible and said maxilla in occlusion; and using each said connective structures to interconnect said members, thereby immobilizing said mandible and said maxilla in occlusion.

In a further aspect of the invention, an apparatus is disclosed for immobilizing a maxilla and a mandible in occlusion, comprising a member including a shaft having a diameter, a proximal end, a distal end; a base removeably affixed to said distal end of said shaft, said base having a diameter which is larger than said diameter of said shaft: a connective structure located at said proximal end; and a removable pointed sheath capable of enclosing said proximal end of said shaft.

The foregoing and other objectives, features, and advantages of the invention will be more readily understood upon consideration of the following detailed description of the invention taking in conjunction with the accompanying drawings.

BRIEF DESCRIPTION OF THE DRAWINGS

FIG. 1 is an enlarged perspective view of a member which is one embodiment of the invention disclosed herein with pointed sheath and base.

FIG. 2 is an enlarged perspective exploded view of the member which is one embodiment of the invention disclosed herein.

FIG. 3 is an enlarged perspective view of the member which is one embodiment of the invention disclosed herein without pointed sheath and with a fastener threaded onto the proximal end of the member.

DETAILED DESCRIPTION OF THE EMBODIMENTS

Figure 4:
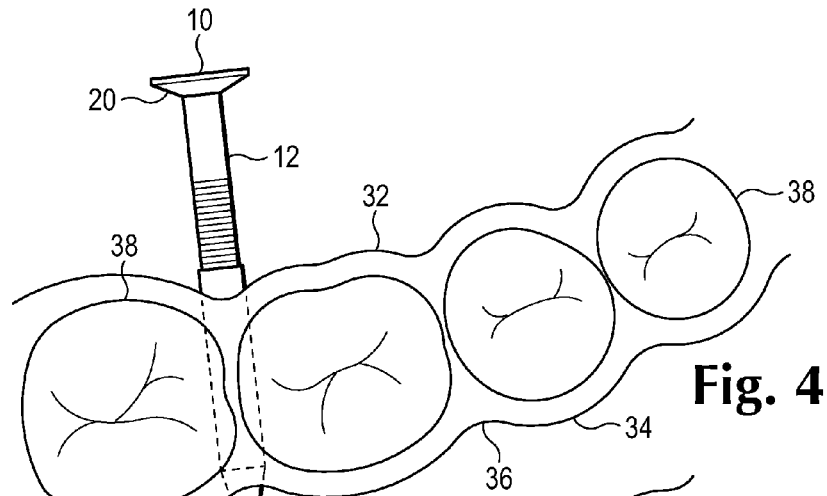
FIG. 4 is an enlarged top-down view of a section of mandible with the member which is one embodiment of the invention disclosed herein with pointed sheath inserting into an interdental space.
Figure 5:
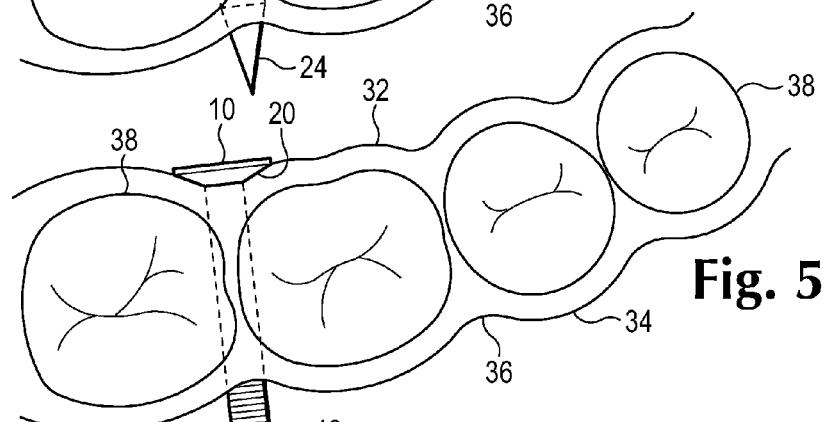
FIG. 5 is an enlarged top-down view of a section of mandible with the member which is one embodiment of the invention disclosed herein inserted into an interdental space with the pointed sheath removed.
Figure 6:
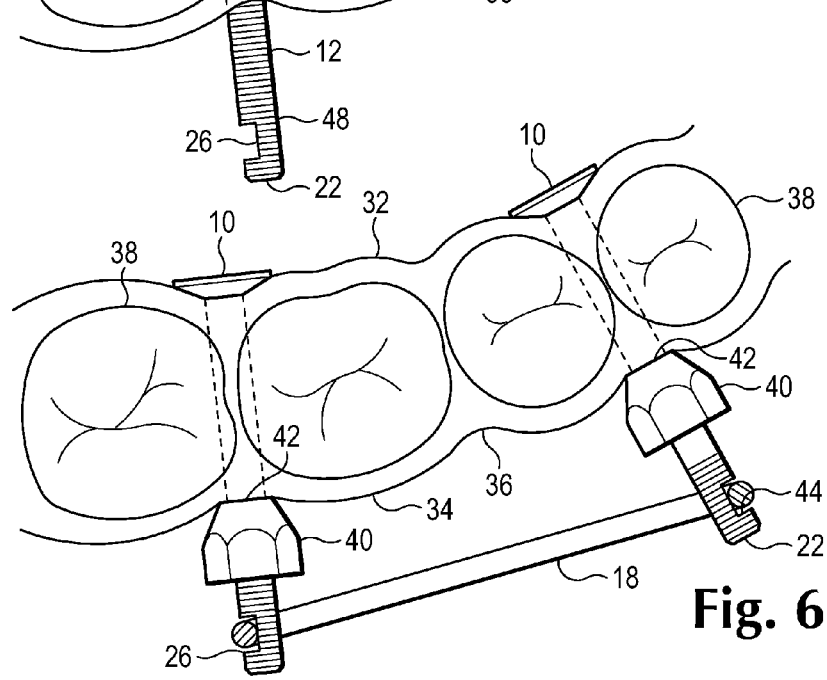
FIG. 6 is an enlarged top-down view of a section of mandible with two members which are one embodiment of the invention disclosed herein inserted into interdental spaces with the pointed sheath removed, a fastener attached, and an elastic band placed in the connective structures.

Mandibular and maxillary bones are made of hard, dense cortical bone into which tooth roots extend and interdental tissue between the teeth themselves. The interdental spaces consist of gingival mucosa and soft tissue and the edge of the alveolar bone, which is spongy and not particularly dense or strong. This interdental tissue has not generally been considered by those of ordinary skill in the art as being strong enough to provide enough fixation strength to accomplish MMF. However, the inventor has discovered and discloses herein methods and apparatus which permit the interdental space to be used for MMF, thus avoiding the inconveniences and dangers of traditional approaches.

Referring now to the drawings which form a part of this disclosure, in one embodiment, a base component 10 made of steel, titanium or plastic, or other such material is attached to the distal end 14 of an elongate member 12. The base component 10 may be threaded onto the member or otherwise removably attached, or it may be permanently attached to or integral to the member. The base component 10 may be a contiguous circular component and it may be attached to a collar 16 which is removably attachable to the elongate member 12. The base 10 has a diameter which is larger than that of the threaded member such that the base extends outward from the distal end of the threaded member, creating a surface 20 that can contact the gingiva. The base may also consist of one or more distal arms which extend outward from the distal end of the threaded member, or any other shape or configuration which creates a surface 20 and is thus capable of spreading force exerted on the threaded member over a larger area. The base 10 may consist of a substantially planar component along with attached ancillary distal arms. The base component may be slightly convex in order to fit securely against the surface of the interdental tissues, or it may be substantially flat.

The proximal end 22 of the elongate member 12 is covered with a pointed sheath 24 which is removably affixed to the member. Beneath the pointed sheath 24 and either integral to or attached to the member 12 is a connective structure 26 which facilitates the connective of two or more elongate members to one another once implanted into the interdental space. The connective structure can be a notch, a groove 44, an eyelet, or anything that is attachable to a screen, elastic band, wire, suture, or the like.

The elongate member can be from about 0.5 mm thick to several millimeters thick, but should not be so thick as to be unduly difficult to fit into the interdental space. It may have a narrower, threaded portion 28 in order for a base 10 having a threaded collar 16 to screw onto it. The elongate member base, pointed sheath, and other components may be made of stainless steel, titanium, or a ceramic or hard plastic.

A surgeon may prefer a different sized elongate member for one patient than for another, depending on patient physiology. An apparatus disclosed herein may be offered in different dimensions in order to offer this choice.

The member 12 may be threaded along its entire length or it may be threaded only at its ends. The middle section 30 may be threaded, may be textured in order to permit it to resist turning in tissue, or it may be smooth. If the base 10 is integral to the member or is attached to the member by some means other than threading, then the member need not be threaded at its distal end. If the fastener 40 is attached to the member 12 through some means other than threading, the proximal end of the member need not be threaded.

The member can be driven through the inter-dental space with manual penetration of the pointed sheath. The member may alternatively be tapped through with a hammer, press, or a clamp. The interdental space 36 may be punctured manually from lingual 32 to buccal surface 34 with the jaws open. Once the sheathed member is lodged in the interdental space, the sharp pointed sheath 24 is removed from the member from the buccal gingival surface 34. This reveals the proximal or buccal end 22 of the member 12. The removal of the pointed sheath 24 avoids the continued presence of a sharp tip on the buccal surface, which may cause patient or surgeon injury.

Alternatively, the member itself may have a pointed proximal end which can be driven through the interdental tissue and then covered so that it does not pose a risk of injury to surrounding tissues. As still another alternate embodiment, instead of a pointed sheath or pointed member end, a needle such as a hollow bore 16 gauge needle may be passed through the interdental space from the buccal side to the lingual side, and a member may be fed into the hollow needle. The needle is then withdrawn after the tip of the member is fed into the needle, drawing the member further through the interdental space.

Once the surface 20 of the base 10 is positioned against the lingual gingival surface 32 of the interdental space 36, outward or lateral tension on the buccal or proximal end 22 of the member will bring the base 10 into close contact with the lingual gingival and/or the teeth. If the base comprises distal arms, they may be gently pulled laterally or buccally to adjust to a position which is approximately perpendicular position to the member, and if there are one or two distal arms, parallel to the alveolar ridge. A substantially round base may be slightly convex to fit tightly into the interdental space.

A fastener 40, which may be a wedge-shaped nut, is then attached to the elongate member. The fastener 40 may be screwed on to the surface of the threads on the portion 48 of the elongate member which protrudes beyond the buccal surface of the alveolar ridge. Alternatively, the fastener 40 may simply slide onto the elongate member 12 and be held in place with a clamp. The fastener 40 is advanced along the elongate member until the fastener contacts the alveolar ridge or gingival, thus securing the member into position. When the base 10 and the fastener 40 have closed upon opposing sides of the alveolus or gingival of the interdental space, they may exert some compressive force on that tissue. The fastener 40 may have an outer diameter which is larger than the outer diameter of the member, resulting in a distal fastener surface 42 which contacts the gingival surface. If the fastener has a substantially conical or wedge shape, contact is permitted between the fastener and the teeth and alveolar ridge on multiple surfaces, enhancing gripping force and the strength of the construct.

A connective structure 26 on the proximal end 22 of the elongate member 12 can be simply a notch or groove 44 in the member into which wires, elastic bands 18, mesh, or other connecters can be inserted. They can also be eyelets, hooks, or any other structure to which an elastic band, wire, or other such structure can be attached.

A member should be implanted in at least one interdental space of the mandible 2 and at least one interdental space of the maxilla 4. Preferably, members are attached in at least two interdental spaces on the upper and lower (maxillary and mandibular) jaws, preferably surrounding the molar up to canine teeth. Members should be implanted in all four quadrants of the alveolus.

Figure 7:
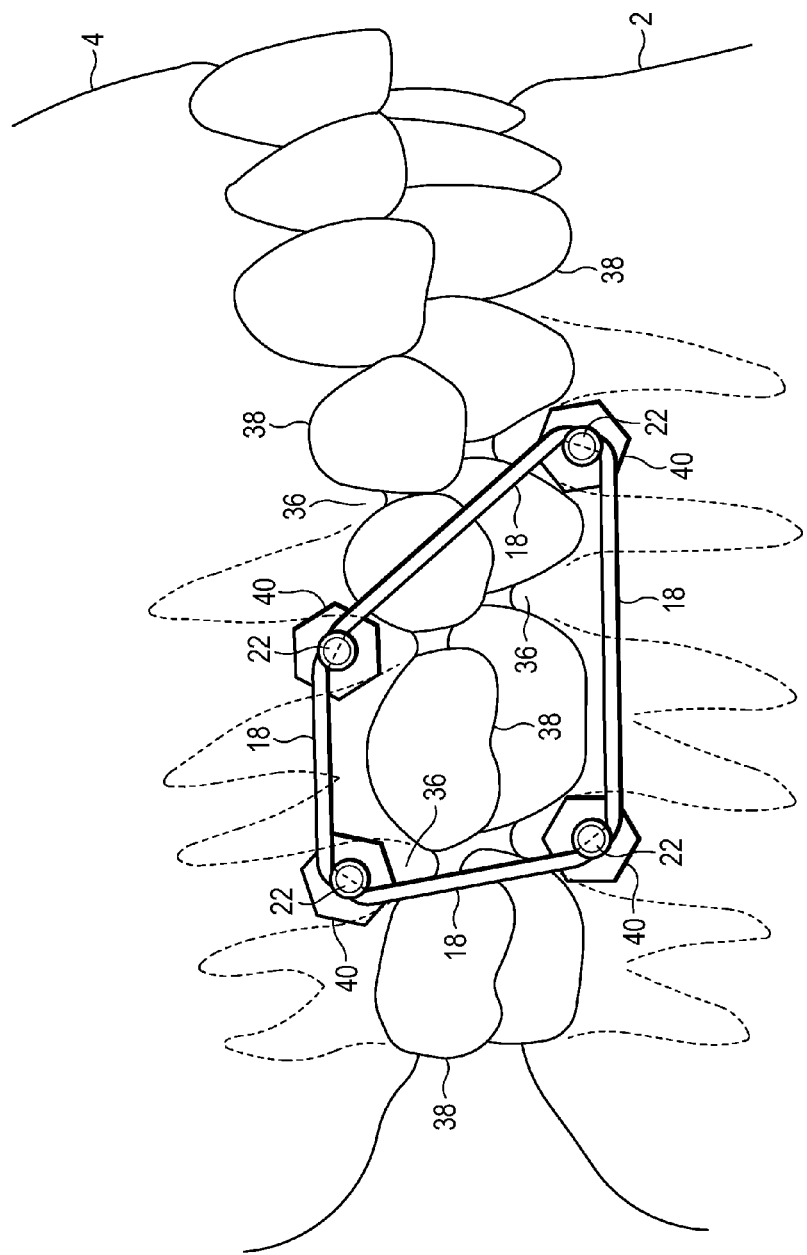
FIG. 7 is an enlarged side view of maxilla and mandible immobilized in dental occlusion by four members which form one embodiment of the invention disclosed herein and an elastic band.

Once this process has been repeated for all four quadrants of the alveolus, inter-maxillary fixation is performed. The patient is placed in desired occlusion. Two disposable mesh screens can be placed on either side, hooking all four members on each side of the mouth, once the patient is in desired occlusion. The mesh is strong enough to hold occlusion due to its multiple wires distributing the tension, but easy to cut with a simple scissors in an emergency. Alternatively, suture, wire, or elastic bands 18 can be fixed over two or more connective structures under tension until the teeth are placed in appropriate occlusion as shown in FIG. 7. In order to prevent unintentional loosening of the maxillo-mandibular fixation wires or bands, an optional eccentric attachment of the elongate member or connective structure can be used. This permits the band or wire to be more secure, or set in a deeper trough, thus preventing inadvertent wire or band release.

Occlusion can be adjusted or remain stable during the healing process. Finally, when using the screen fixation, the occlusion can actually be modified by advancing the mandible and fixating in the advanced position.

The device can also be worn nightly for fracture stabilization or as a sort of oral appliance, with the screens or elastic bands applied nightly for mandibular advancement or stabilization in sleep apnea.

The terms and expressions which have been used in this specification are intended to describe the invention, not limit it. The scope of the invention is defined and limited only by the following claims.

What is claimed is:

1. A method of immobilizing a mandible and a maxilla in occlusion, comprising: (a) providing at least two members, each said member comprising a shaft having a diameter, a proximal end, and a distal end, a base affixed to said distal end, said base having a diameter which is larger than said diameter of said shaft, and each said member further comprising a connective structure located at said proximal end, each said proximal end of each said member further comprising a removable pointed component; (b) inserting one said member through a first interdental space within said mandible; (c) inserting another said member through a first interdental space within said maxilla; (d) removing each said removable pointed component; (e) attaching a connective structure to the proximal end of each said shaft; (f) placing said mandible and said maxilla in occlusion; and (g) using said connective structures to interconnect said members, thereby immobilizing said mandible and said maxilla in occlusion.

2. The method of claim 1 further comprising the step of compressing interdental tissue between said base and said connective structure.

3. The method of claim 1 further comprising inserting an additional member through a second interdental space within said maxilla and inserting an additional member through a second interdental space within said mandible.

\* \* \* \* \*